United States Patent [19]

Weiss

[11] Patent Number: 4,998,178

[45] Date of Patent: Mar. 5, 1991

[54] ADJUSTABLE, CONDUCTIVE BODY STRAP

[75] Inventor: John W. Weiss, Austin, Tex.

[73] Assignee: Minnesota Mining and Manufacturing Company, St. Paul, Minn.

[21] Appl. No.: 539,859

[22] Filed: Jun. 8, 1990

[51] Int. Cl.⁵ .............................................. H05F 3/02
[52] U.S. Cl. .................................................... 361/220
[58] Field of Search ............... 361/212, 220, 223, 224; 24/170, 188

[56] References Cited

U.S. PATENT DOCUMENTS

| | | | |
|---|---|---|---|
| 3,063,447 | 3/1961 | Kirsten | 128/134 |
| 4,038,726 | 8/1977 | Takabayashi | 24/198 |
| 4,540,271 | 9/1985 | Rakov | 355/3 R |
| 4,720,765 | 1/1988 | Weiss | 361/220 |
| 4,782,425 | 11/1988 | Breidegam | 361/212 |
| 4,845,585 | 7/1989 | Weiss | 361/220 |

OTHER PUBLICATIONS

Desco Technical Bulletin, P-2005 06/87.

Primary Examiner—A. D. Pellinen
Assistant Examiner—Brian Johannssen
Attorney, Agent, or Firm—Donald M. Sell; Walter N. Kirn; John C. Barnes

[57] ABSTRACT

An adjustable conductive body strap which is readily adjustable and which utilized an elastomerically extensible electrically conductive band held together and adapted to be joined to a grounding cord which makes 360° electrical contact and continuity with the body is desired and this is accomplished by having one end of the band fastened by contact with a conductive plate which has teeth which penetrate the second end.

6 Claims, 3 Drawing Sheets

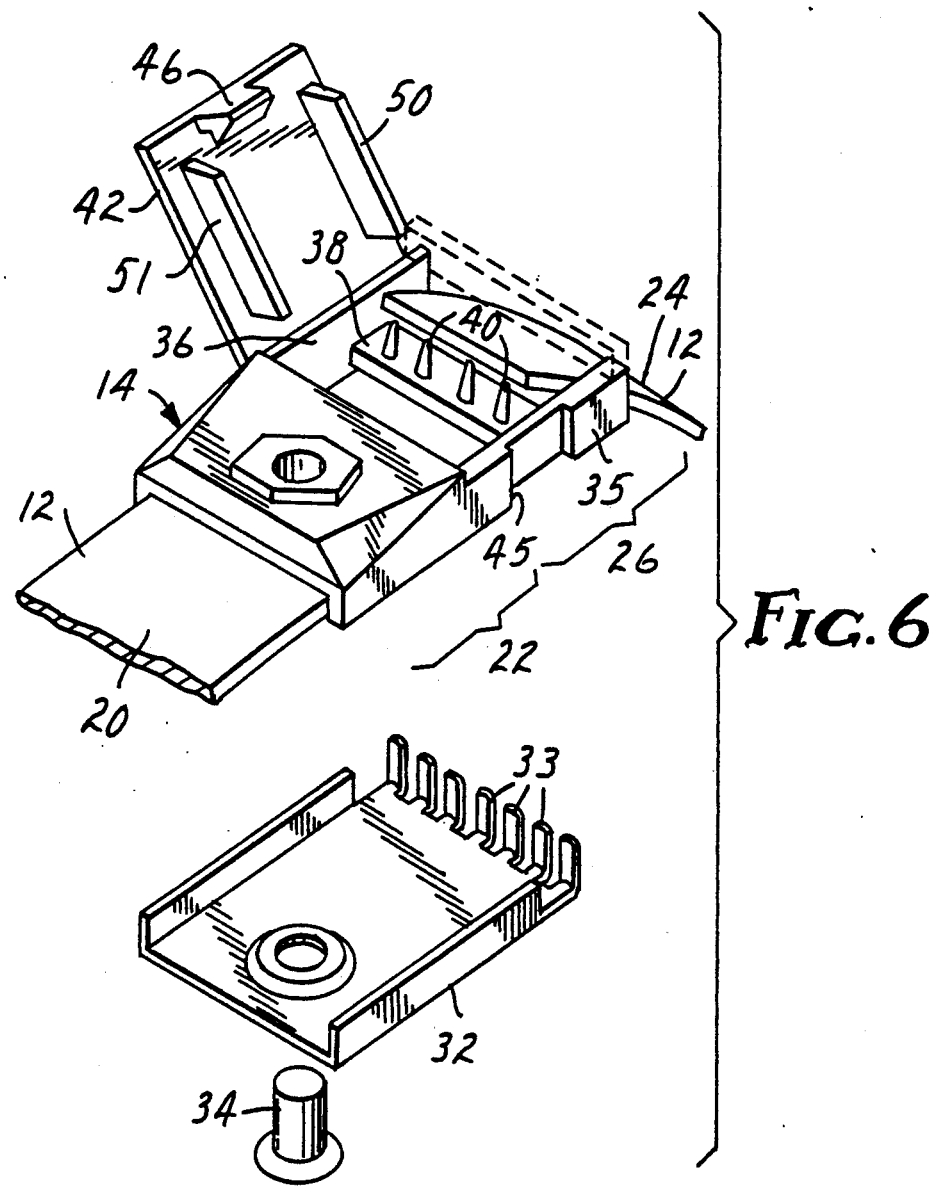
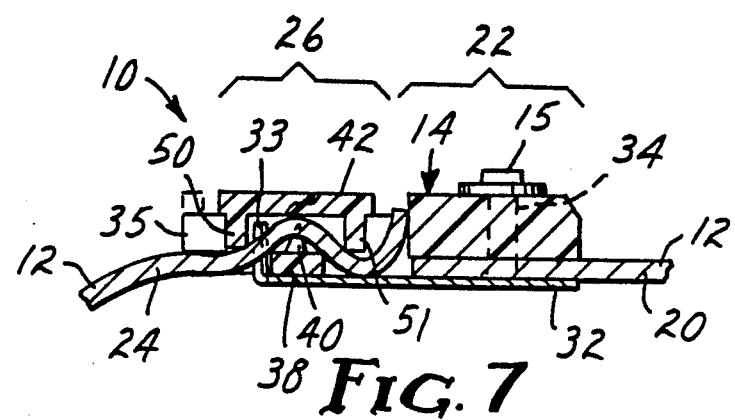

ADJUSTABLE, CONDUCTIVE BODY STRAP

The present invention relates generally to electrically conductive body straps and more particularly to elastic electrically conductive wrist straps which provide 360 degrees of electrical contact and continuity, and which are adjustable.

BACKGROUND OF THE INVENTION

The presence of electrostatic charges and the subsequent discharge of the same can create significant problems in certain industries, particularly where explosive materials are involved and in electronic manufacturing or assembly plants. Individuals working in an everyday work environment commonly may develop thousands of volts of electrostatic charge potential by, as an example, walking across carpeting or moving dissimilar objects against each other. An individual, or object, so charged presents a severe hazard in the above identified environments. In an explosive materials environment the danger is inherently obvious. In the electronic integrated circuit (component) industry, the charged individual or object, may discharge near or through a static charge sensitive electronic component. For example, an individual who is electrostatically charged may hold a static charge sensitive component and then lay the component on a surface, e.g., a grounded work surface, at a different potential from the individual. At the instant of contact, a potential difference of thousands of volts exists across the component, from the electrostatically charged individual to the grounded work surface. The current passing through or near, due to the electric field generated, may damage the component. The damage caused to the component may cause it to fail immediately or, worse, could degrade the operating characteristics or the reliability of the component. The result is either expensive rework or, worse, the existence of substandard or subreliable equipment in the field.

A device which is used to help control the electrostatic charge buildup on a person is a body strap or wrist strap to be worn by the individual. The body straps are conductive on the surface contacting the skin surface and provide for an electrical connection point. An electrical ground cord may then be connected to the strap connecting the strap to an electrical ground potential, preferably through a predetermined limiting resistance usually built into the connector or the cord itself. So connected, such a body strap operates by draining any accumulated electrostatic charge on the individual to ground before the electrostatic charge buildup reaches dangerous levels.

One prior art body strap is described in U.S. Pat. No. 4,398,277, Christiansen et al, Conductive Elastomeric Body Strap. Christiansen et al describe a body strap which is constructed from a band of fabric formed into a closed loop to encircle a body part, e,.g., wrist, to which it is to be connected. The fabric is electrically conductive on the interior surface of the closed loop contacting the skin. A mechanical connection mechanism holds the loop of fabric in a fixed predetermined size. An electrical connection mechanism provides for an electrical connection between the conductive inner surface of the fabric to an electrical grounding cord which may be attached to the strap. The fabric is elastomeric to enable the body strap to expand to slip over the hand and still be snug around the wrist.

In the body strap described in Christiansen et al, the opposite ends of the fabric are permanently secured in the mechanical connector. The body of the connector has projections which grip the fabric and hold the fabric in the connector when the cover is secured. Thus, the resultant body strap formed is a fixed closed loop size. Since the fabric has a limit on the degree of its elastic nature, a range of sizes of closed loops for the body strap must be provided. This results in the necessity of stocking a plurality of differing sizes of body straps. Further, the elastomeric characteristics of the fabric generally means a fixed "life" of use of the fabric before its elastomeric or electroconductivity characteristics begin to break down. Since the fabric is secured in the connector at the factory, the replacement of the fabric requires replacement of the entire body strap.

The Charge-Guard 2200 series of static control wrist straps manufactured by Minnesota Mining and Manufacturing Company, St. Paul, Minnesota is constructed generally as described in Christiansen et al (Charge-Guard is a registered trademark of Minnesota Mining and Manufacturing Company, St. Paul, Minnesota). In the Charge-Guard static control wrist straps, the ends of the projections 32, in Christiansen et al, are sonically welded after the fabric is in place to "Mushroom" the ends of the projections in order to ensure that the fabric is secured in the connector.

U.S. Pat. No. 4,577,256, Breidegam, Woven Stretchable Grounding Strap, describes a wrist strap designed to be used to control electrostatic charge accumulations. The Breidegam strap has a clasp which allows its size to be adjusted. The adjustable clasp avoids the need to manufacture two or more models of the strap for different sized wrists. This does require that the strap be individually adjusted to fit snugly around the wrist of the individual wearer. If inadvertently or intentionally maladjusted, proper electrostatic protection may not be achieved. In the Breidegam strap, one end of the fabric is permanently secured into the clasp and held by plate and a rivet. Thus, one end of the fabric is fixed at the factory for the entire life of the strap. The second end of the fabric is engaged in the clasp by a pivotally mounted gate which when closed "jams" the fabric holding it in place, optionally with teeth to help the securing of the fabric. Typically, a pivotally mounted "jam" or "wedge" as is described in Breidegam is referred to as an "overcenter" device. These devices operate by wedging the fabric between the jam member and a reaction member by using an eccentric pivot with a relatively long jam operating lever to gain the necessary leverage for the jam to work. One problem in a strap as described in Breidegam is that it does not allow for full 360 degree electrical contact with the skin and the fabric is electrically connected only at one end. Since electrical contact is only provided to the external ground cord from the one fixed end of the fabric, any charge contacting the inner surface of the fabric must travel around the strap in one direction only until reaching the fixed end. This requires, in some instances, a charge to follow only one path to travel almost entirely around the fabric before being connected to a ground strap. Since the electrical conductivity of the fabric, for several reasons, is typically the weakest link in a wrist strap grounding system, along with the fabric to skin contact, such one way only conductivity is a serious problem. Another problem with the Breidegam strap is that the pivotally mounted nonconductive clasp does not lend itself to economical manufacture. Because of the forces involved, the pivot points are required to be quite sturdily built.

Earlier U.S. Pat. No. 4,845,585 discloses an adjustable wrist strap where the band is laid into a recess 36 in the molded part above the back plate 32. As the cover 42 was closed over the strap and a bar having spikes 40, the cover caused the strap to be forced into more intimate contact with back plate 32. The spikes 40 also held the strap from pulling free of the cover. This band affords 360 degree contact with the wrist.

Other prior art includes an earlier wrist band available from Simco Company, Inc, Hatfield, PA 19440, referred to as the Simco Trustat ™ lay-in band which band had a strip of conductive material with one end terminated in an opening in a molded head, which had a slotted opening near one edge in the bottom wall and the conductive metal back plate had a folded edge which penetrated this slotted opening in the bottom wall and a serrated edge on the folded end of the metal plate pinched the end of the strip against the top wall of the head when a fastening rivet for the cord snap was placed through the metal back plate, the bottom of the head, the strip and the top surface of the head to engage the cord snap and hold the members together. This wrist strap also included a tail portion having a projecting lower plate with a raised bar transversely thereof which was positioned between two ribs on a hinged cover to place an S-bend in the strip and hold the other end of the strip to the body of the structure. There did not appear to be any contact between the second end of the strip and the metal back plate at the tail portion of the connector.

The present invention is a modification of the band of U.S. Pat. No. 4,845,585, an improvement in that it undoubtedly makes the 360 degree contact and electrical continuity between the band and the connector with the wrist.

SUMMARY OF THE INVENTION

The present invention provides a body strap useful for the control of electrostatic charge accumulation. The body strap is adapted to fit the wrist of the user and provides for full 360 degree electrical contact and continuity with the skin, provides easy one-time, or repeated, adjustment by the individual user for trouble-free secure holding of the fabric ends and for the replaceability of the fabric only, if desired.

Thus, the present invention provides for an adjustable, conductive body strap. The strap has a strip of material having a first end and a second end. The strip of material is electrically conductive on at least one surface, is elastomerically extensible in its longitudinal direction and is of at least a length to enable the strip of material to encircle a body part.

A mechanical connector receives the first end and the second end of the strip of material to form a closed loop with the strip of material with the conductive surface formed toward the interior of the closed loop. The mechanical connector has a body having a head portion and a tail portion. The head portion receives the first end of the strip of material and the a tail portion receives the second end of the strip material. The head portion has a recess which receives the first end of the strip of material, the recess being formed with a plurality of spikes upon which the strip of material is impaled and secured. The tail portion of the mechanical connector has a plate over which the second end of the strip of material is passed. The plate has a plurality of raised teeth or spikes formed on its edge upon which the strip of material may be impaled after the strip of material has been pulled to fit snugly around the body part. The tail portion of the connector can also have a bar with spikes to help secure the strip. This tail portion of the mechanical connector further has a hinged cover which may be secured over the spikes of the plate and the bar trapping the strip of material thereon. The plate is a conductive back plate which also is positioned in the recess of the head and holds the strip against the spikes formed on the head at the base of the recess or bottom surface of the head. An electrical connection mechanism is coupled to the strip of material for providing a connection point for an electrical cable capable of connecting the conductive body strap to ground. The back plate of the connector also forms a second cover and when secured to the head portion of the mechanical connector by the cord connector fastener, secures the first end of the strip of material upon the spikes. Preferably, the spikes formed on the other end of the back plate make positive contact with the second end of the strip of material providing full 360 degree electrical continuity and full 360 degree electrical contact with the skin. Preferably, the hinged cover has transverse ridges spaced to pass on either side of the teeth formed on the plate when the hinge cover is closed. Preferably, the transverse ridges maintain the strip of material in electrical contact with the spikes on the metal cover plate when the hinged cover is closed. Preferably, the hinged cover of the mechanical connector is hingeably attached at one side wall of the tail portion and is preferably, secured by means of a releasible hook to the other wall.

BRIEF DESCRIPTION OF THE DRAWINGS

The foregoing advantages, construction and operation of the present invention will become more readily apparent from the following drawings and accompanying description in which:

FIG. 6 is an exploded isometric view of the mechanical connector used in the adjustable conductive body strap of the present invention; and FIG. 7 is a cross-sectional view of the mechanical connector of the adjustable, conductive body strap of the present invention showing the mechanical connector in the closed position.

DESCRIPTION OF THE PREFERRED EMBODIMENTS

Figure 1:
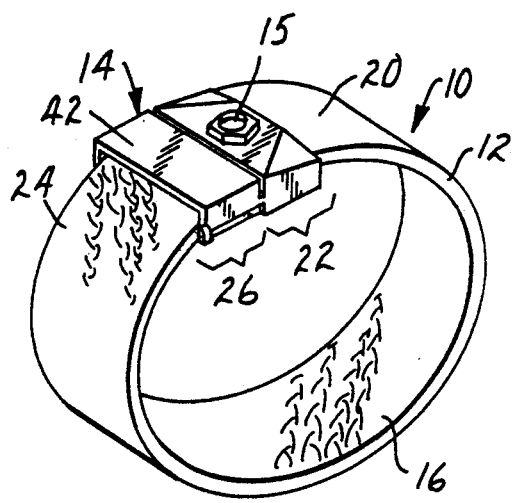
FIG. 1 is an isometric view of the body strap of the present invention.

The adjustable, electrically conductive body strap 10 is illustrated in FIG. 1. The body strap 10 is formed into a closed loop designed to fit snugly around a portion of the body, e.g., a wrist or an ankle. The loop is formed by a strip of material 12 formed into a loop by connector 14. Connector 14 forms both the mechanical connection holding both ends of the strip of material 12 and the electrical connection mechanism or snap fastener 15 providing a point for external connection of the body strap 10 to a ground potential.

The interior surface 16 of the strip of material 12 is electrically conductive and should intimately contact the skin of the individual wearer of the body strap 10 when it is in position. Thus, electrostatic charges accumulating on the person of the wearer can be transported from the skin of the wearer to the conductive interior surface 16 of the body strap 10 transported to connector 14 in two directions and made available for conduction to ground through the snap fastener 15 for connecting a grounding cord. Strip of material 12 may be formed of any suitable elastomeric electrically conductive material such as a woven or knitted fabric to form the band portion of the body strap 10. In a preferred embodiment, strip of material 12 is a knit fabric containing both elastomeric and electrically conductive fibers as described in Christiansen et al. Optionally, however, strip of material 12 could also be constructed from a stretch weave material such as is described in Breidegam identified above.

A first end 20 of the strip of material 12 is mechanically secured in a head portion 22 of a molded body of the connector 14. The second end 24 of the strip of material 12 is adjustably secured in a tail portion 26 of connector 14.

Figure 4:
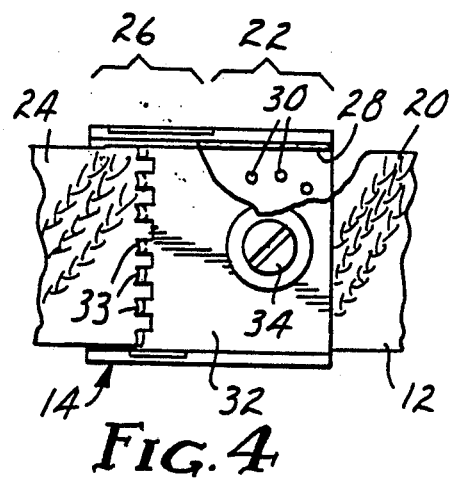
FIG. 4 is a bottom view of the mechanical connector partly broken away to illustrate the detail under the metal cover plate.
Figure 5:
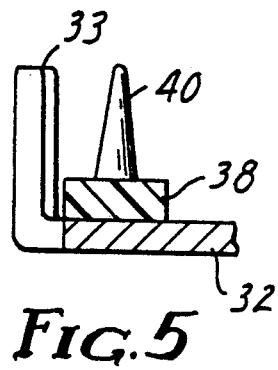
FIG. 5 is a cross-section of the tail portion of the mechanical connector.
Figure 2:
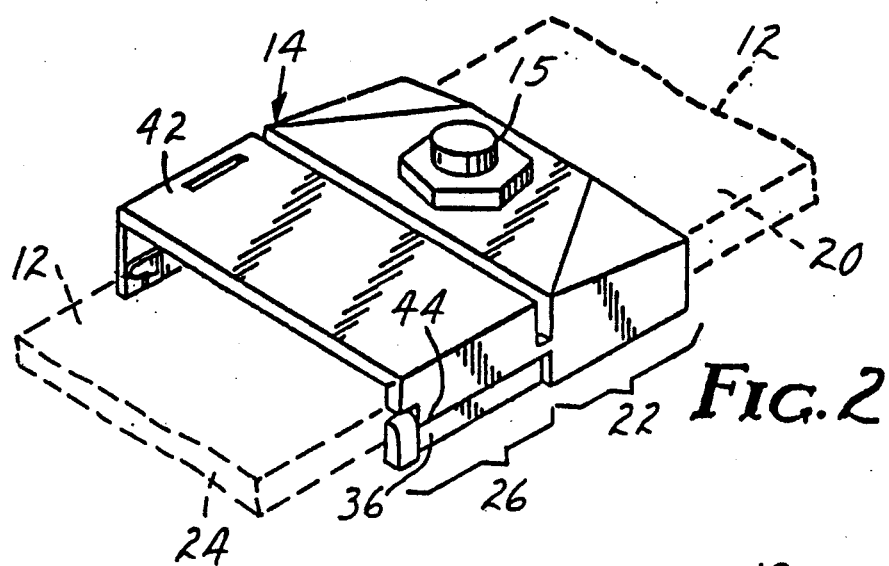
FIG. 2 is an enlarged isometric view of the mechanical connector in a closed position.
Figure 3:
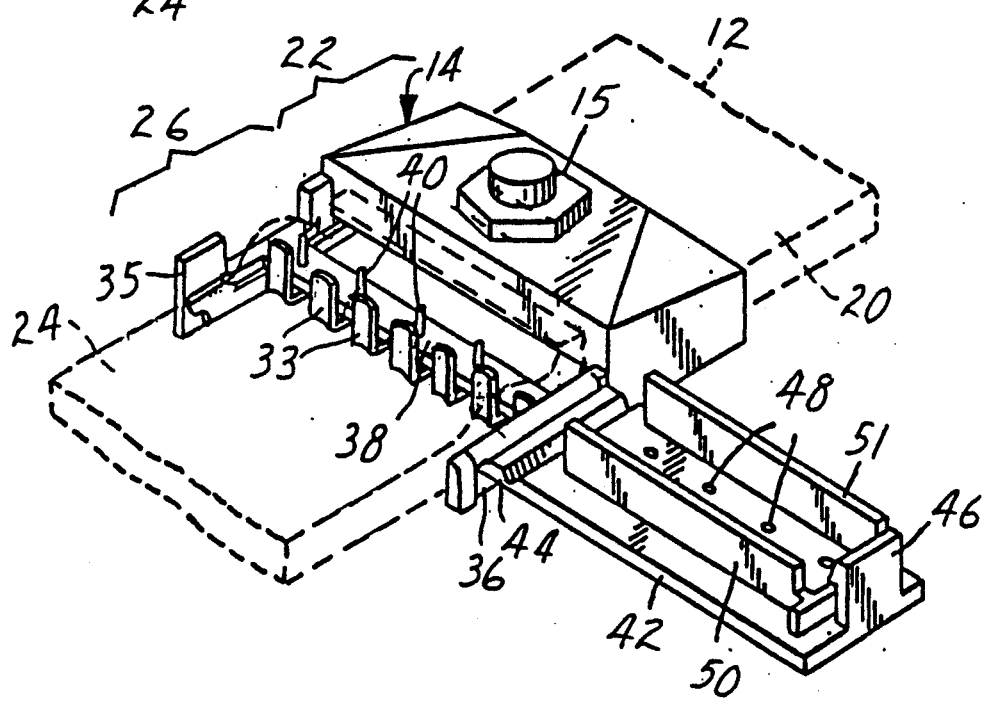
FIG. 3 is an enlarged isometric view of the mechanical connector with the cover in an open position and the strip of material illustrated in phantom lines.

The details of connector 14 are more readily illustrated in FIGS. 2 and 3. The first end 20 of the strip of material 12 is secured in the head 22 of the connector 14. Secured in this manner the first end 20 is semi-permanently secured in that only disassembly of connector 14 can release first end 20 of the strip of material 12 from the connector 14. It is anticipated that body strap 10 can be shipped from the factory with the first end 20 of the strip of material 12 semi-permanently secured in the head 22 of connector 14. This can be shown in better detail in FIG. 4 where the first end 20 of the strip of material 12 is formed into a recess 28 of the head 22 of the connector 14. There the strip of material 12 is impaled upon a plurality of spikes 30 designed to secure first end 20 the strip of material 12 within the connector 14 when a metallic back plate 32 which is secured in the connector 14 through a stud 34 and its snap fastener 15. Stud 34 as well as snap connector 15 are metallic allowing for electrical conductivity from the interior surface 16 of the strip of material 12 to the metal plate 32, to the snap fastener 15 and, of course, subsequently by external cord (not shown) to a ground potential.

The plate 32 is formed as illustrated most clearly in FIG. 6 is formed of metal to fit into the body of the connector beneath the head portion 22 and to extend into the tail portion 26. It has upwardly bent side flanges to strengthen the plate, which flanges fit within the walls of the head portion forming a recess for the one end 20 of the strip of material 12 and a hole to receive the shaft 34 of the rivet for the snap fastener 15. On the extended end of the plate 32, which extends into the tail portion 26, the plate is formed with upstanding teeth or spikes 33 which are spaced along the edge of the plate 32. These teeth 33 are formed with rounded upper ends to penetrate the strip 12 and are shaped to reduce the tendency to cut or abrade any of the fibers in the strip while making good electrical contact with the conductive fibers therein.

Again referring to FIGS. 2 and 3, the second end 24 of the strip of material 12 is placed in a recess formed between two spaced walls 35 and 36 in the tail portion 26 of connector 14. The tail portion 26 of connector 14 contains a transverse bar 38 upon which are mounted a plurality of spikes 40 extending outwardly from the transverse bar 38. The second end 24 of the strip of material 12 is passed over the teeth 33 and the transverse bar 38 extending between the walls 35 and 36 of the tail portion 26.

The strip is then drawn until the strip of material 12 is securely tightened around the body part with which it is to be utilized. When the strip of material 12 is suitably tight, a cover 42, hinged as at 44 to the side wall 36 of the tail portion 26 is closed over the second end of the strip. The cover 42 is provided with a hook 46 at the end opposite the hinge to secure the cover 42 to the side wall 35. The second wall 35 is provided with a recess 45, see FIG. 6, to receive the hook 46 and permit the detent on the end of the hook to lock beneath the wall 35 or other suitable projection. Preferably, hinged cover 42 contains a plurality of recesses 48 which cooperate with and receive the tips of spikes 40 when hinge cover 42 is in a closed position. The receiving of the tip of spikes 40 in recesses 48 will help prevent spikes 40 from bending, and subsequent release of the strip of material 12 from connector 14. Also preferably, hinged cover 42 has spaced transverse ridges 50 and 51 positioned on the cover to be positioned one on each side of the transverse bar 38 to force the strip of material 12 into more intimate electrical contact with the teeth 33 on the back plate 32 and with the spikes 40 on the bar 38 as illustrated from the cross-sectional view of FIG. 7. The bar 38 also serves to hold the wall 35 and 36 in fixed spaced relationship and counteracts the force on the cover to press the strip material 12 onto the teeth 33 of the plate member and reduce the tendency of the plate member to move. FIG. 7 also illustrates the impaling of the strip of material 12 upon teeth 33 as well as the electrical contact between back plate 32 and both the first end 20 and the second end 24 of the strip of material 12 forming full 360 degree electrical continuity around body strap 10 and skin contact.

Optionally, and preferably, second end 24 of the strip of material 12 will be trimmed at least flush with the edge of hinged cover 42 as also illustrated in FIG. 7 such that no electrically conductive surface is present on the exterior surface of body strap 10.

The material forming the body of the connector 14 is a plastic material, preferably one that is static dissipative. In general, a material is static dissipative if it has a surface resistivity of between $10^8$ and $10^{14}$ ohms per square. Examples of material which could be utilized and which are static dissipative include, for example hygroscopic nylon and carbon loaded polypropylene.

Thus, it can be seen that there has been shown and described a novel adjustable, conductive body strap. It is to be recognized and understood, however, that various changes, modifications and substitutions in the form and in the details of the present invention may be made by those skilled in the art without departing from the scope of the following claims.

I claim:

1. An adjustable, conductive body strap, comprising:
   a strip of material having a first end and a second end, said strip of material being electrically conductive on at least one surface, being elastomerically extensible in its longitudinal direction, and being of at least a length to enable said strip of material to encircle a body part;
   a molded mechanical connector receiving said first end and said second end of said strip of material to form a closed loop with said strip of material with said at least one surface toward the interior of said closed loop, said mechanical connector having a head for receiving said first end and having a projecting tail portion formed with spaced wall members between which is received said second end of said strip;

said head of said mechanical connector having a recess receiving said first end of said strip of material, said recess being formed with a plurality of spikes upon which said strip of material is impaled and secured;

said tail portion of said mechanical connector having a cover hinged to one of said wall members and having a detent to fasten to the other of said wall members when pivoted over said second end of said strip; and a conductive plate member positioned against said interior surface of the loop for pressing said one end of said strip against the head and for supporting the second end between said wall members, said plate having teeth formed in the end thereof and positioned between said wall members to penetrate said strip and make good electrical contact with said strip and restrict said second end from pulling free of said cover.

2. An adjustable, conductive body strap as claimed in claim 1 wherein said connector has a fastener penetrating said plate ember, the first end of the strip and the head to secure the plate to the head and form a snap connector for a grounding cord.

3. An adjustable, conductive body strap as claimed in claim 1 wherein connector cover has a pair of transverse ridges spaced to be positioned on opposite sides of the teeth on said plate member to hold the strip onto said teeth.

4. An adjustable, conductive body strap as claimed in claim 2 wherein connector cover has a pair of transverse ridges spaced to be positioned on opposite sides of the teeth on said plate member to hold the strip onto said teeth.

5. An adjustable, conductive body strap as claimed in claim 1 wherein a bar is positioned transverse to said tail portion for aiding the plate to counterbalance the force of the cover urging the strip against the teeth of the plate member, which bar is positioned between transverse ridges on the cover positioned to be on opposite sides of the teeth of the plate member and the bar.

6. An adjustable, conductive body strap as claimed in claim 1 wherein the plate member is formed of metal.

* * * * *